US009414774B2

(12) United States Patent
Korner et al.

(10) Patent No.: US 9,414,774 B2
(45) Date of Patent: Aug. 16, 2016

(54) METHOD AND SYSTEM FOR WITHDRAWING BODY FLUID

(75) Inventors: Stephan Korner, Cham (CH); Rainer Jaeggi, Thalwil (CH); Patrick Griss, Otelfingen (CH); Emad Sarofim, Hagendorn (CH); Irio Guiseppe Calasso, Arth (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 2175 days.

(21) Appl. No.: 11/539,675

(22) Filed: Oct. 9, 2006

(65) Prior Publication Data
US 2007/0118051 A1 May 24, 2007

Related U.S. Application Data

(63) Continuation of application No. PCT/EP2005/003423, filed on Apr. 1, 2005.

(30) Foreign Application Priority Data

Apr. 10, 2004 (EP) .................................... 04008691

(51) Int. Cl.
*A61B 5/00* (2006.01)
*A61B 5/15* (2006.01)

(52) U.S. Cl.
CPC ................... *A61B 5/1411* (2013.01)

(58) Field of Classification Search
CPC .................................................. A61B 5/1411
USPC ........... 600/583, 584, 573; 606/181, 182, 183
See application file for complete search history.

(56) References Cited

U.S. PATENT DOCUMENTS

| 5,879,311 | A | | 3/1999 | Duchon et al. |
| 5,879,367 | A | * | 3/1999 | Latterell et al. ............... 606/181 |
| 5,964,718 | A | | 10/1999 | Duchon et al. |
| 6,066,103 | A | * | 5/2000 | Duchon et al. ................ 600/583 |
| 6,071,250 | A | * | 6/2000 | Douglas et al. ............... 600/583 |
| 6,143,164 | A | | 11/2000 | Heller et al. |
| 6,283,982 | B1 | | 9/2001 | Levaughn et al. |
| 6,306,152 | B1 | | 10/2001 | Verdonk et al. |
| 6,332,871 | B1 | | 12/2001 | Douglas et al. |
| 6,464,649 | B1 | | 10/2002 | Duchon et al. |

(Continued)

FOREIGN PATENT DOCUMENTS

| EP | 1 407 712 A1 | 1/2003 |
| EP | 1 304 075 A1 | 4/2003 |

(Continued)

*Primary Examiner* — Brian Szmal
*Assistant Examiner* — H. Q. Nguyen
(74) *Attorney, Agent, or Firm* — Bose McKinney & Evans LLP

(57) ABSTRACT

A system and method for carrying out the withdrawal of body fluid with as little body fluid as possible visible to the user at the end of the process. The present invention provides a pressure piece for exerting pressure on a body part. The pressure piece is moved relative to a support for the body part, and in the final phase of fluid withdrawal, the compressive or resistive force of the pressure piece on the body part is reduced in order to avoid the escape of body fluid from the puncture site. The support results in a defined positioning of the body part that rests against it for the lancing process, whereas the relative movement of the pressure piece enables an additional increase in pressure and thus an improved collection of fluid.

45 Claims, 2 Drawing Sheets

(56) References Cited

U.S. PATENT DOCUMENTS

| | | | |
|---|---|---|---|
| 6,607,218 B2 | 8/2003 | Sakazaki et al. | |
| 6,969,359 B2 | 11/2005 | Duchon et al. | |
| 7,288,073 B2 * | 10/2007 | Effenhauser et al. | 600/584 |
| 7,582,063 B2 * | 9/2009 | Wurster et al. | 600/584 |
| 2002/0002344 A1 * | 1/2002 | Douglas et al. | 600/583 |
| 2002/0029058 A1 | 3/2002 | Levaughn et al. | |
| 2002/0168290 A1 | 11/2002 | Yuzhakov et al. | |
| 2003/0018282 A1 | 1/2003 | Effenhauser et al. | |
| 2003/0050627 A1 | 3/2003 | Taylor et al. | |
| 2003/0050655 A1 | 3/2003 | Roe | |
| 2003/0212344 A1 * | 11/2003 | Yuzhakov et al. | 600/583 |
| 2003/0233112 A1 * | 12/2003 | Alden et al. | 606/181 |
| 2004/0215224 A1 * | 10/2004 | Sakata et al. | 606/181 |
| 2004/0236251 A1 * | 11/2004 | Roe et al. | 600/583 |
| 2005/0085839 A1 * | 4/2005 | Allen et al. | 606/181 |

FOREIGN PATENT DOCUMENTS

| | | |
|---|---|---|
| EP | 1 360 933 A1 | 11/2003 |
| WO | WO 03/007819 A1 | 1/2003 |
| WO | WO 03/009759 A1 | 2/2003 |
| WO | WO 03/022130 A2 | 3/2003 |
| WO | WO 03/022331 A2 | 3/2003 |

* cited by examiner

METHOD AND SYSTEM FOR WITHDRAWING BODY FLUID

RELATED APPLICATIONS

This is a continuation application of International Application PCT/EP2005/003423 filed Apr. 1, 2005 which claims priority to EP04008691.0, filed Apr. 10, 2004.

BACKGROUND

The present invention relates to a method and a system for withdrawing body fluid, and in particular to such a system and method which includes a pressure piece that is in contact with the skin during the withdrawal process.

Methods and collecting systems for small amounts of body fluids are used to the greatest extent by diabetics for blood sugar self-monitoring that is typically performed several times daily as part of a normoglycaemic-oriented insulin treatment. In order for laymen to carry out the required steps in a simple and rapid manner, it is desirable to provide so-called "integrated systems" in which blood collection and analysis is carried out in a combined manner in one unit. In order to collect capillary blood, it is necessary to puncture the skin, but is desirable to do so in a manner that the puncture pain and scar formation is minimized to the extent possible.

One such integrated system, among others, is described in WO2001089383, which discloses an elastomeric compression unit used as a pressure piece. The perforation device comprises a cannula that is inserted into the compressed skin area and remains there to collect body fluid. Apart from requiring adequate transfer of blood to an analytical zone, it can also be problematic for the user hygienically and psychologically that some of the collected blood remains visible on the skin surface after the measurement.

It would be desirable to avoid the above-noted disadvantages and to enable an optimized collection of body fluid with simple handling.

SUMMARY OF THE INVENTION

The present invention provides a system and method to carry out the withdrawal of body fluid in such a manner that as little body fluid as possible, namely, blood or tissue fluid, is visible to the user at the end of the process.

The present invention provides a pressure piece for exerting pressure that is moved relative to a support for the body part, and during (and preferably in the final phase) of fluid withdrawal, the compressive force of the pressure piece on the body part is reduced in order to avoid the escape of body fluid. The body part rests against the support and has a defined position relative thereto for the lancing process, whereas the relative movement of the pressure piece enables an additional increase in pressure and thus an improved collection of fluid. A central aspect is that the fluid flow assisted by pressure increase is stopped by a permanent reduction in pressure during the final phase of the withdrawal process, thus avoiding an unintentional or excessive escape of fluid onto the skin surface. Consequently, almost no fluid or blood is visible on the skin surface after collection. This is more hygienic in everyday environments and is also helpful for the user from a psychological perspective. It is also advantageous that the puncture wound opens and closes by increasing and decreasing the compressing force of the pressure piece. This also reduces the sensation of pain because the lancing member can remain at a suitable position in a wound opened by the pressure piece.

The body fluid is advantageously withdrawn by the lancing member as part of the collecting unit. In this connection, the lancing member is preferably withdrawn from the area of the body part either during or after the pressure reduction such that the puncture wound is not exposed under liquid pressure.

One embodiment provides that the pressure piece is moved towards the support against a resisting force by pressing on the body part such that the body part is also compressed. Alternatively, it is also possible that the pressure piece is moved towards and/or moved away from the body part resting against the support by means of a positioning drive.

In another exemplary embodiment, the compressive force of the pressure piece can be lowered by relaxing a pretensioning element and in particular a pretensioned spring acting against the pressure piece. It is also conceivable to use a force element designed, for example, as a plunger coil to regulate the compressive force.

In order to impart a tactile signal to the user to indicate the completion of the withdrawal process, it is advantageous when the pressure piece is moved away from the body part at the end of the fluid withdrawal. Another embodiment involves reducing the pressure on the body part by retracting the pressure piece through an opening of the support into a position that is screened from contact by the body part.

Advantageously, the pressure piece delimits a free puncture area for the lancing member.

According to a further embodiment of the invention, the compressive force exerted by the pressure piece is controlled for a defined withdrawal of fluid. The control occurs passively by means of an optionally user-defined empirical presetting for the withdrawal duration, or actively by means of a sensory detection of the collected volume or of the actual flow rate of the body fluid. The latter enables a feedback adaptation of the time course of the compressing force.

A defined initial force of the pressure piece can be set by generating a release signal to activate the lancing process when the pressure piece reaches a preset position or when the support is touched. It is also possible that in a stop position of the pressure piece or of the support, a release signal is generated to activate the lancing process. It can also be activated by the user himself or automatically by a countdown after the release signal. This should in any case ensure that the lancing process is not triggered unexpectedly for the user.

In order to reduce the puncture pain during collection it is advantageous when the lancing member is inserted to a defined lancing depth into the body part and then is retracted into a collecting position at a smaller lancing depth.

The handling is especially simplified by the fact that a detection unit is coupled with the collecting unit to analyze the body fluid. In this case, it is particularly advantageous when the body fluid is taken up and transported to the collecting unit by a capillary transport channel.

Different pressure pieces can be optionally used for an anatomical adaptation to the body part to which they are applied. In addition to circular pressure pieces, other contours such as linear or punctiform contours or combinations thereof can be used. This also assists the accurate positioning of the body part in addition to assisting the pressure build-up, and the blood collection can be additionally monitored with regard to the decisive parameters. In this respect, it may also be advantageous when the pressure piece is deformable in a rubber elastic manner and in particular consists of a soft or elastomeric material. This also improves the adaptation of the pressure piece to the body part.

For the fluid collection, it is advantageous when a puncture area of the body part is bulged or compressed or stretched by lateral deflection under the primary pressure of the pressure piece.

With regard to the device, the pressure piece can be moved relative to a support for the body part in order to exert pressure, and during the fluid withdrawal, an actuator reducing the compressive force is operatively connected to the pressure piece.

In another exemplary embodiment, the pressure piece can be moved relative to a support for the body part in order to exert pressure and a control unit is provided to control the compressing force of the pressure piece in accordance with the desired withdrawal of fluid.

BRIEF DESCRIPTION OF THE DRAWINGS

The above-mentioned aspects of the present invention and the manner of obtaining them will become more apparent and the invention will be better understood by reference to the following description of the embodiments of the invention taken in conjunction with the accompanying drawings, wherein.

Corresponding reference numerals indicate corresponding parts throughout the several views.

DETAILED DESCRIPTION

Figure 1:
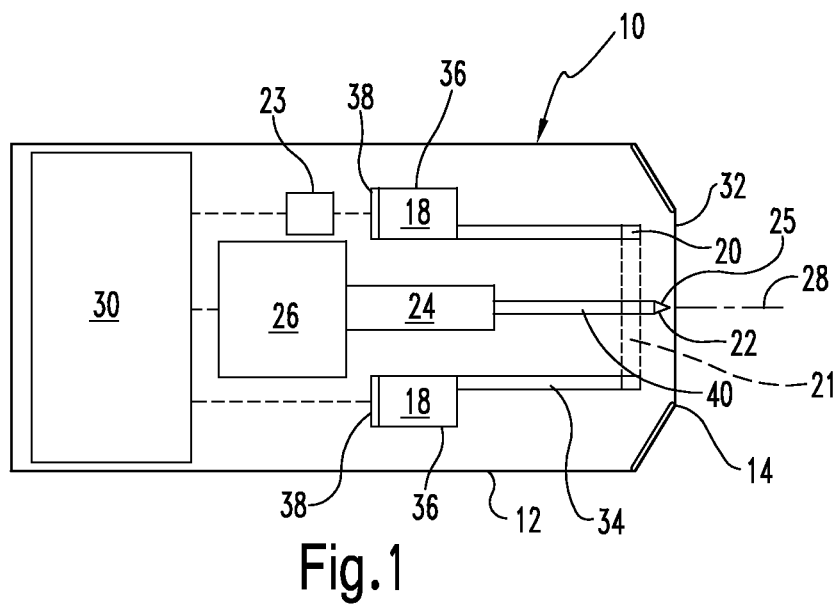
FIG. 1 is a diagrammatic view of a device for withdrawing and analysing blood.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The device shown in the drawing is designed as a hand-held device 10 for combined blood withdrawal and analysis. It includes an instrument housing 12 with a support 14 for a body part 16 of a user, a pressure ring 20 that can be moved by means of an actuator 18 relative to the support 14. A collecting unit 40 for blood withdrawal is provided with a lancing member 22, and a detection unit 24 for blood analysis is coupled to the collecting unit 40. Instead of a circular ring 20, a pressure piece 21 in the form of a bar configured to press down on the body part linearly or a strut configured to press down on the body part in the punctiform manner can be provided.

The lancing movement of the collecting unit 40 with the lancing member 22 is carried out by a lancing drive 26 in a lancing axis 28 which extends through an opening 32 of the support 14. A processor unit 30 is provided for the process control of the actuator 18 and of the lancing drive 26 as well as to evaluate the measuring results.

The pressure ring 20 can be moved by a linear guide 24 coaxially to the lancing member 22 along the lancing axis 28. During this process, the pressure ring 20 can be pressed back by pressing on the body part 16 against the force of a return spring 36 of the actuator 18 so that, as a reaction, the pressure on the body part increases during blood withdrawal. In order to subsequently enable a pressure reduction during the final phase of blood withdrawal, the actuator has a movable spring support 38 to relax the spring element 36. Alternatively, it is also possible that the actuator 18 includes, e.g., a curve-controlled positioning drive to control the course of movement of the pressure ring 20 (not shown). As a further alternative, it is also possible to provide a force element 23 as shown in FIG. 1 to regulate the compressive force.

The collecting unit 40 has a capillary transport channel 25, also referred to herein as capillary 25, in order to automatically transport the body fluid removed at the collection site to the detection unit 24. This can be formed by an open rim capillary groove in order to simplify the manufacture. In order to detect glucose content in the blood, the detection unit 24 is, for example, aligned onto a suitable test field, for example, a reflection photometric unit. Such measuring systems with disposable test elements for blood sugar self-monitoring for diabetics are well-known.

Figure 2:
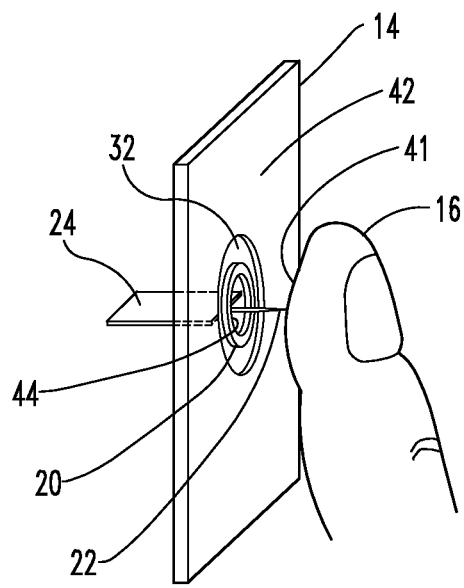
FIG. 2 is a fragmentary perspective view illustrating the arrangement of a lancing unit, a pressure ring and a positioning surface of the device according to FIG. 1.

The basic arrangement for direct blood collection from the body part 16 is illustrated in FIG. 2. Blood is preferably removed from the finger pad 41 which is applied to the facing positioning surface 42 of the support 40 in the area of the opening 32. The pressure ring 20 can be moved through the opening 32 while the lancing member 22 as a capillary-active needle tip can be lanced through the ring opening 44 into the finger pad 41.

Figure 3:
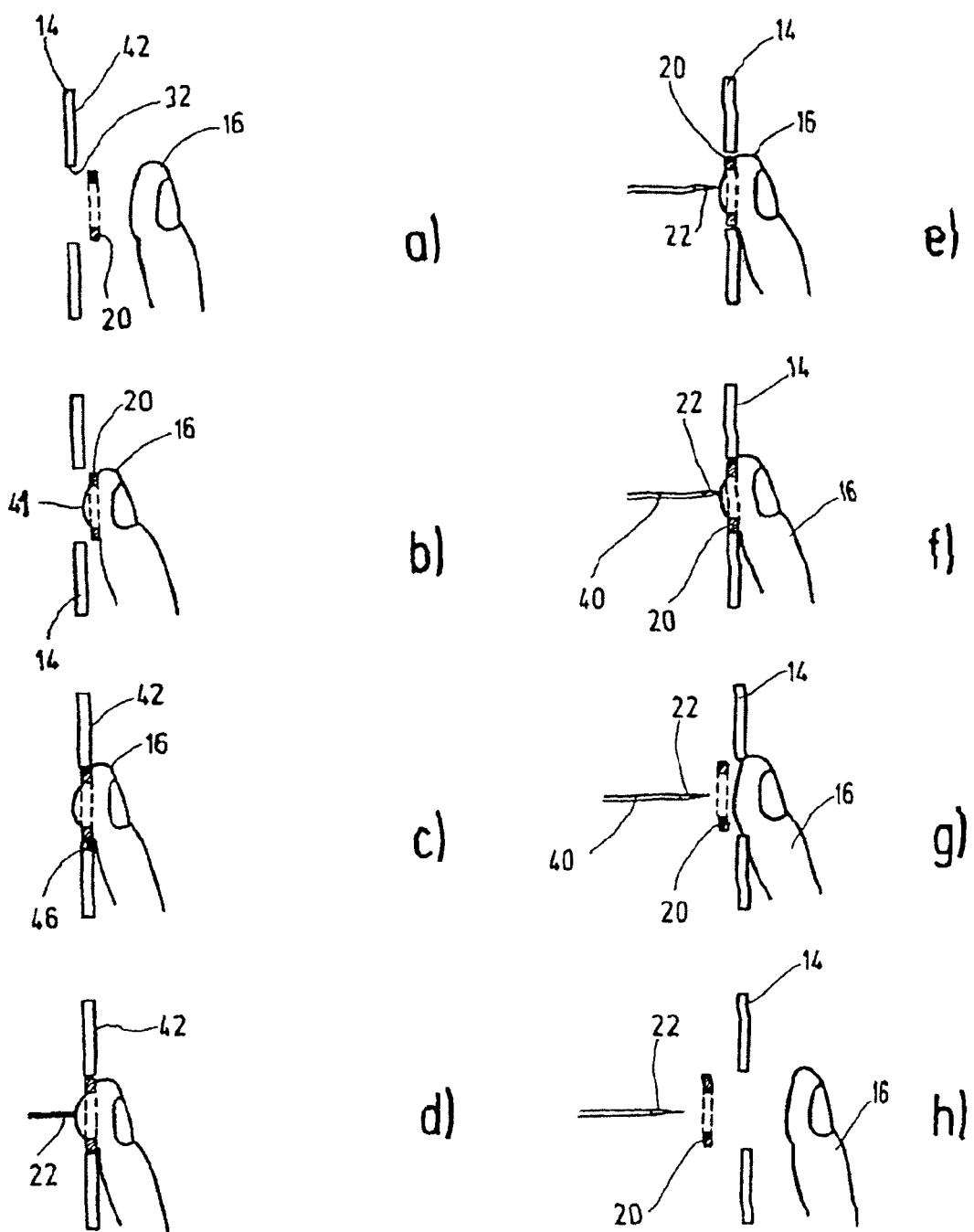
FIGS. 3a to h are fragmentary side views showing various positions of the elements shown in FIG. 2 during blood withdrawal.

FIG. 3 shows the sequence of the individual process steps for blood collection. According to FIGS. 3a and b the pressure piece 20 extended out of the instrument housing is moved towards the support 14 against a resisting force by pressing from the body part 16. Under the increased pressure, the body part 16 is bulged in the area of the finger pad or finger tip 41 so that additional blood accumulates.

When the positioning surface 42 is reached, a release signal is generated by a touch sensor 46 (FIG. 3c), whereupon the user triggers the lancing process. The lancing member 22 is then rapidly inserted to a defined lancing depth (FIG. 3d) and then retracted or pulled back into a collecting position at a smaller lancing depth (FIG. 3e). In this position the lancing member is in the area of the skin (optionally also just above it) while the open puncture channel fills with blood. In this process, the blood flows automatically into the transport channel due to capillary forces (FIG. 3f). In this phase, the counter force exerted by the ring 20 may be modulated or varied in order to control the flow of blood.

After removing a defined amount of blood which can be actively detected or empirically determined on the basis of an allocated withdrawal period, the compressing force of the pressure ring 20 is steadily or gradually reduced in order to prevent blood escaping from the puncture wound, such that no blood is visible on the skin surface. For this purpose the pressure ring 20 is retracted through the opening 32 of the support 14 into a position in the housing that is screened from contact by the body part 16. In this process, the collecting unit 40 is also completely retracted from the area of the body part 16 (FIG. 3g), which ends the blood collection. In the end position shown in FIG. 3h, the pressure ring 20 is positioned inside the housing behind the support 14. The collecting unit 40 is also retracted inside the housing so that the analysis can be carried out. The movement of the pressure ring 20 away from the body part 16 also provides a discernable and tactile signal to the user that the collection process has been completed.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of using an analytical instrument for withdrawing blood from a body part, comprising:
    moving a pressure piece relative to a support which contacts the body part to exert pressure on the body part with the pressure piece;
    inserting a lancing member into the body part, wherein the lancing member includes a capillary to collect blood;
    withdrawing blood through the capillary with a collecting unit;
    using the analytical instrument to reduce the compressive force of the pressure piece on the body part to avoid forming a drop of blood on the skin surface of the body part.

2. The method of claim 1, wherein the reducing the compressive force takes place in the final phase of fluid withdrawal.

3. The method of claim 1, wherein the lancing member is removed from the body part during or after the pressure reduction.

4. The method of claim 1, further comprising pressing the body part against the pressure piece, wherein the pressure piece is moved towards the support against a resisting force.

5. The method of claim 1, wherein a positioning drive moves the pressure piece towards or away from the body part.

6. The method of claim 1, wherein the compressive force of the pressure piece is lowered by relaxing a pretensioning element comprising a pretensioned spring acting against the pressure piece.

7. The method of claim 1, wherein the compressive force of the pressure piece is regulated by a force element.

8. The method of claim 1, wherein the pressure piece is moved away from the body part at the end of fluid withdrawal.

9. The method of claim 1, wherein the pressure piece is retracted through an opening of the support into a position that is screened from contact by the body part in order to reduce the pressure.

10. The method of claim 1, wherein the pressure piece delimits a free puncture area for the lancing member.

11. The method of claim 1, wherein the compressive force exerted by the pressure piece is controlled as a function of the amount, rate, or duration of fluid withdrawal.

12. A method of using an analytical instrument for withdrawing blood from a body part, comprising:
    moving a pressure piece relative to a support which contacts the body part to exert pressure on the body part with the pressure piece;
    inserting a lancing member into the body part to create a puncture;
    withdrawing blood with a collecting unit;
    controlling the compressive force exerted by the pressure piece on the body part for a defined withdrawal of blood and thereafter using the analytical instrument to reduce the compressive force exerted by the pressure piece in a permanent manner without increase; and then
    moving the lancing member away from the body part with substantially no blood being visible on the skin surface near the puncture.

13. The method of claim 12, wherein the control occurs by one of a user-defined presetting for the withdrawal duration, a detection of the collected volume, or of the actual flow rate of the body fluid.

14. The method of claim 12, further comprising generating a release signal to activate the lancing process when the pressure piece reaches a preset position or when the support is touched.

15. The method of claim 12, further comprising generating a release signal to activate the lancing process when the pressure piece or the support is in a stop position.

16. The method of claim 12, wherein the lancing member is inserted to a defined lancing depth into the body part and then is retracted into a collecting position at a smaller lancing depth.

17. The method of claim 12, further comprising coupling a detection unit with the collecting unit to analyse the body fluid.

18. The method of claim 12, further comprising transporting the body fluid by a capillary transport channel of the collecting unit.

19. The method of claim 12, further comprising selecting the pressure piece from a plurality of different pressure pieces, wherein the method is adapted to the anatomy of the body part.

20. The method of claim 12, further comprising bulging or stretching the body part in a puncture area under the pressure of the pressure piece.

21. A system for withdrawing blood from a body part, comprising:
    a pressure piece configured to apply pressure to a body part and having an actuator operably connected thereto;
    a lancing member configured for insertion into the body part and including a capillary to collect blood;
    a support configured to contact the body part;
    a collecting unit to withdraw blood; and
    the pressure piece being movable relative to the support in order to exert pressure on the body part, wherein the actuator is configured to reduce the compressive force of the pressure piece in a permanent manner without increase after removing an amount of blood, whereby substantially no blood is visible on a skin surface near a puncture created by the lancing member after the lancing member is retracted from the body part.

22. The system of claim 21, wherein the lancing member is formed on the collecting unit.

23. The system of claim 21, wherein the pressure piece is configured to be moved towards the support against a restoring force of the actuator by pressing the body part against the pressure piece.

24. The system of claim 21, wherein the actuator comprises a pretensioning element that further comprises a spring resting under pretension against the pressure piece.

25. The system of claim 21, wherein the actuator comprises a movable support to relax the pretensioning element.

26. The system of claim 21, wherein the actuator comprises a curve-controlled positioning drive for the movement of the pressure piece.

27. The system of claim 21, wherein the support comprises a positioning surface to which to apply the body part, the positioning surface being provided with an opening for the passage of the pressure piece.

28. The system of claim 21, wherein the pressure piece is formed as a ring and the lancing member is configured to be lanced through an opening in the ring into the body part.

29. The system of claim 21, wherein the pressure piece is formed by at least one bar configured to press down on the body part linearly or by a strut configured to press down on the body part in a punctiform manner.

30. The system of claim 21, wherein the pressure piece is elastically deformable.

31. The system of claim 21, further comprising a signal generator that is activated when a preset position is reached or when the support or the pressure piece is touched or reaches a stop position in order to generate a release signal for the activation of the lancing member.

32. The system of claim 21, wherein the collecting unit is operatively connected with a detection unit configured to analyze the body fluid.

33. The system of claim 21, wherein the collecting unit comprises a capillary transport channel to transport the body fluid.

34. A method of withdrawing blood from a body part with a device of the type having a housing, a lancing opening formed in the housing and which defines a support for the body part, a lancing member which is extendable through the lancing opening during operation of the device, and a movable pressure piece positioned adjacent the opening, the method comprising:
  arranging the pressure piece such that it can be contacted from outside of the housing by a body part;
  exerting pressure on the pressure piece with the body part during which the pressure piece moves and provides a resistive force against the body part;
  after beginning the step of exerting pressure on the pressure piece with the body part, inserting the lancing member into the body part to a lancing depth;
  withdrawing blood from the body part;
  retracting the pressure piece inside of the housing; and
  removing the body part from the lancing device after the step of retracting the pressure piece within the opening, wherein substantially no blood is visible on the skin surface near the puncture created by the lancing member.

35. The method of claim 34, further comprising, after the inserting step, partially retracting the lancing member to a collecting position in which the tip of the lancing member is positioned at or below a skin surface.

36. The method of claim 35, further comprising completely retracting the lancing member from the body part.

37. The method of claim 34, further comprising contacting the support with the body part.

38. The method of claim 37, further comprising triggering the inserting of the lancing member when the body part contacts the support.

39. The method of claim 34, further comprising regulating the amount of the resistive force provided by the pressure piece against the body part as a function of the quantity of body fluid withdrawn, rate of body fluid withdrawal, or duration of body fluid withdrawal.

40. The method of claim 39, wherein the body part is in contact with the support and the pressure piece during the regulating of the amount of resistive force provided by the pressure piece.

41. The method of claim 34, further comprising providing the pressure piece in the form of a ring.

42. The method of claim 34, wherein the pressure piece initially extends from the lancing opening.

43. The method of claim 34, wherein the resistive force provided by the pressure piece against the body part is reduced as the withdrawal of body fluid proceeds.

44. The method of claim 43, wherein the reduction in the resistive force provided by the pressure piece concludes with the pressure piece being removed from contact with the body part, whereby a tactile signal is provided to the user that the body fluid withdrawal is complete.

45. The method of claim 43, wherein the reduction in the resistive force is gradual.

\* \* \* \* \*